US011648297B2

(12) United States Patent
Lux et al.

(10) Patent No.: US 11,648,297 B2
(45) Date of Patent: May 16, 2023

(54) BIORESPONSIVE PARTICLES

(71) Applicant: Board of Regents, The University of Texas System, Austin, TX (US)

(72) Inventors: Jacques Lux, Dallas, TX (US); Robert F. Mattrey, Dallas, TX (US); Annie Y. Heble, Dallas, TX (US)

(73) Assignee: Board of Regents, The University of Texas System, Austin, TX (US)

(*) Notice: Subject to any disclaimer, the term of this patent is extended or adjusted under 35 U.S.C. 154(b) by 341 days.

(21) Appl. No.: 16/429,026

(22) Filed: Jun. 2, 2019

(65) Prior Publication Data

US 2019/0367902 A1 Dec. 5, 2019

Related U.S. Application Data

(60) Provisional application No. 62/679,762, filed on Jun. 1, 2018.

(51) Int. Cl.
| | |
|---|---|
| *A61K 9/00* | (2006.01) |
| *A61K 38/44* | (2006.01) |
| *C12N 11/14* | (2006.01) |
| *A61K 49/22* | (2006.01) |
| *A61K 38/50* | (2006.01) |
| *A61K 38/51* | (2006.01) |
| *A61K 38/48* | (2006.01) |
| *A61K 51/08* | (2006.01) |
| *A61K 51/12* | (2006.01) |
| *C12N 9/08* | (2006.01) |
| *C12N 9/96* | (2006.01) |
| *B82Y 5/00* | (2011.01) |

(52) U.S. Cl.
CPC ............ *A61K 38/446* (2013.01); *A61K 38/44* (2013.01); *A61K 38/4813* (2013.01); *A61K 38/50* (2013.01); *A61K 38/51* (2013.01); *A61K 49/221* (2013.01); *A61K 49/222* (2013.01); *A61K 49/223* (2013.01); *A61K 49/225* (2013.01); *A61K 51/088* (2013.01); *A61K 51/1244* (2013.01); *C12N 9/0065* (2013.01); *C12N 9/96* (2013.01); *C12N 11/14* (2013.01); *B82Y 5/00* (2013.01); *C12Y 111/01006* (2013.01); *C12Y 113/12005* (2013.01); *C12Y 115/01001* (2013.01); *C12Y 304/17011* (2013.01); *C12Y 305/01001* (2013.01); *C12Y 404/01011* (2013.01)

(58) Field of Classification Search
CPC .................................................... A61K 38/446
See application file for complete search history.

(56) References Cited

U.S. PATENT DOCUMENTS 8,507,606 B2 * 8/2013 Grate .................... C12N 11/06
525/54.1

OTHER PUBLICATIONS

Chang, Intracellular Implantation of Enzymes in Hollow Silica Nanospheres for Protein Therapy: Cascade System of Superoxide Dismutase and Catalase, Small, 2014, 10(22), 4785-4795.*
Kim, Single enzyme nanoparticles in nanoporous silica: a hierarchial approach to enzyme stabilization and immobilization, Enzyme and Microbial Technology, 2006, 39, 474-480.*

* cited by examiner

*Primary Examiner* — Paul W Dickinson
(74) *Attorney, Agent, or Firm* — Richard Aron Osman

(57) ABSTRACT

Shielding enzymes are made by modifying the enzyme surface with silica precursors and then depositing silica to a desired thickness while retaining biological activity of the enzyme.

20 Claims, 4 Drawing Sheets

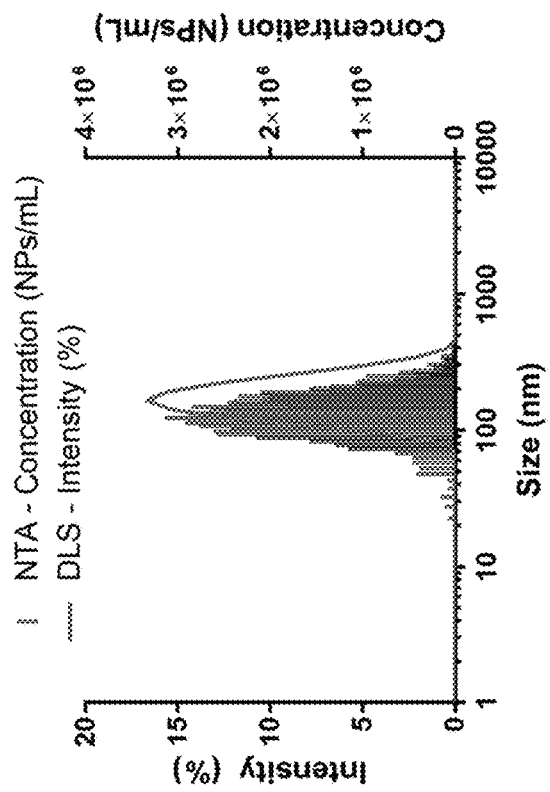
Fig. 5
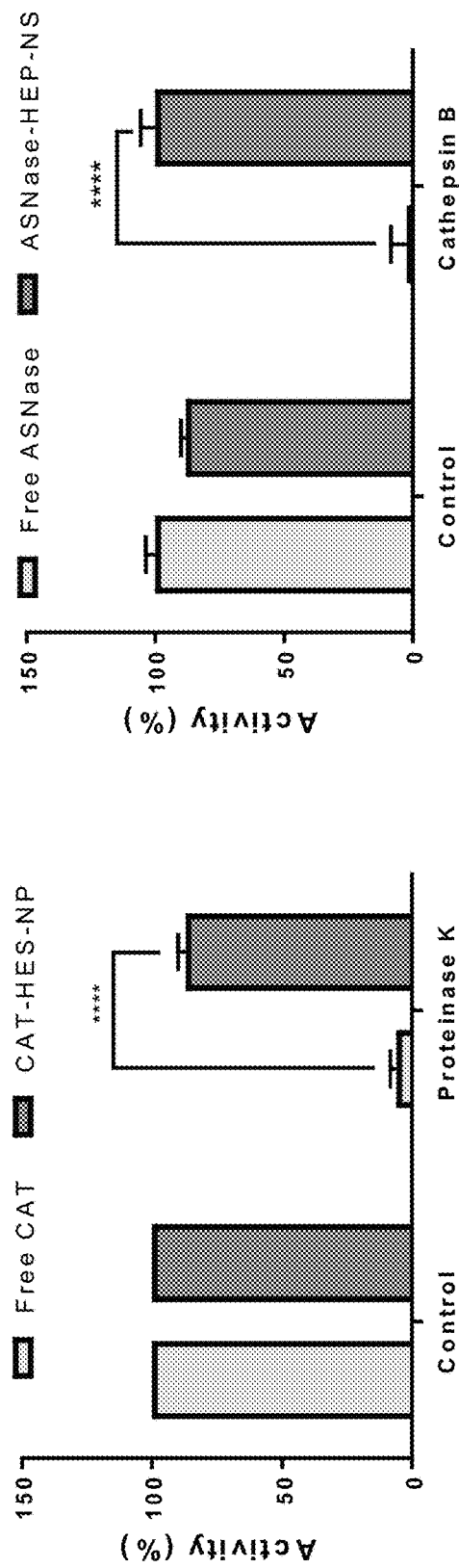
Fig. 6A
Fig. 6B

BIORESPONSIVE PARTICLES

This invention was made with government support under Grant Number UL1TR001105 awarded by the National Institutes of Health (NIH). The government has certain rights in the invention.

INTRODUCTION

Acute lymphoblastic leukemia (ALL) is the most common childhood cancer accounting for more than 25 percent of all pediatric cancers in the U.S. Unfortunately, 30 percent of children have immune responses to one of the most effective treatments for ALL that is highly allergenic. These immune responses either render the treatment completely ineffective, particularly when children relapse, or worse, immediately threaten the life of the child, or both. Because this treatment is essential for permanently curing children of ALL, it is critical that novel strategies be devised to completely eliminate these immune reactions.

In an aspect, our invention provides for incorporating this treatment enzyme in ultrasmall particles that are porous to asparagine, but at the same time, prevent the entry of large components of the immune system, will protect a child from immune reactions, but will effectively deplete asparagine. This will not only increase the enzyme's functional life in the child's body, but will also eliminate the harmful immune responses. By creating this nanoscale "force field" around the cancer treatment enzyme, it can do its job to cure the children of cancer much more safely.

Prior enzyme shielding strategies include the silica coating of single enzymes for industrial use (US2014/0127778) and the passive accumulation of enzymes inside hollow silica shells (US2016/0243262). Neither approach is optimal. The first produces ultrasmall nanoparticles; however, shielding is suboptimal as enzyme activity decreases by 90 percent at room temperature in one week, and even faster in vivo and at body temperature, since plasma contains protein-cleaving enzymes to weaken the shield and deactivate the enzyme. The second approach has particle size and enzyme loading limitations. Since it is produced using two templates of markedly different sizes to create hollow silica shells with relatively large pores to allow entry of enzymes prior to closing the pores, particles cannot be made smaller than 100-200 nanometers. This relatively large size forces them to stay in blood speeding their removal by the liver and spleen, and limiting their ability to reach the cellular microenvironment in sufficient quantities to adequately fight cancer or provide enzymes to cells that so desperately need them. Further, since they are filled by suspending them in aqueous solutions of the enzyme, they can only trap the amount that can be dissolved without precipitation limiting enzyme loading. Low enzyme activity requires higher dosages to achieve the enzyme activity needed for the desired application, increasing toxicity.

Our invention allows continuous fine-tuning of enzyme activity per particle and particle size. Because we begin by attaching anchors on each enzyme molecule without affecting its function that serve as seeds upon which silica can deposit, we can control how many enzyme molecules we can put together in each particle to provide full control of number of enzyme molecules per particle and ultimately particle size.

RELEVANT LITERATURE

Trogler et al., US20150273061

Yang et al., in situ synthesis of porous silica nanoparticles for covalent immobilization of Enzymes, Nanoscale 2012, 4, 414

Ortac I, Simberg O, Yeh Y S, Yang J, Messmer B, Trogler W C, Tsien R Y, Esener S. Dualporosity hollow nanoparticles for the immunoprotection and delivery of nonhuman enzymes. Nano Lett. 2014; 14(6):3023-32. doi: 10.1021/nl404360k. PubMed. PMID: 24471767; PMCID: PMC4059531.

Olson E S, Ortac I, Malone C, Esener S, Mattrey R. Ultrasound Detection of Regional Oxidative Stress in Deep Tissues Using Novel Enzyme Loaded Nanoparticles. Adv Healthc Mater. 2017; 6(5). doi: 10.1002/adhm.201601163. PubMed. PMID: 28081299; PMCID: PMC5516546.

Aspects of this disclosure were presented at Bioengineering Seminar at UT Arlington. Bioresponsive Particles for the Detection of Disease by Ultrasound. Nov. 1, 2017.

SUMMARY OF THE INVENTION

The invention provides methods and compositions for shielding enzymes with silica. We use enone groups to decorate enzymes, which then allow the facile reaction of the silyl amine derivative to obtain silyl groups on the enzyme which acts as the seed for the growth of the siloxane scaffold around the enzyme (nanoporous silica network/shell that protects the enzymes).

The invention provides a silica modified enzyme comprising an enzyme covalently decorated with enone groups, around which is grown a siloxane scaffold, to form a hybrid enzyme-silica nanoparticle (TIES-NP). Loading the silica modified enzyme into a silica nanoshell protects the enzyme, such as from inactivation by proteolysis In an aspect the invention provides a method of making a silica-modified enzyme comprising the steps of: a) reacting an acrylic compound (acryloyl derivative) with amine groups of an enzyme to covalently decorate the enzyme with enone groups; and b) coupling a silyl amine to the enone groups to covalently decorate the enzyme with silyl groups, forming a silica-modified enzyme.

In embodiments:
  the acrylic compound comprises an acryloyl group and an N-hydroxysuccinimide group, such as N-acryloxysuccinimide or acrylate-polyethyleneglycol N-hydroxysuccinimide; and/or
  the silyl amine is comprises a silyl ether group and an amine group, such as 3-aminopropyl trimethoxysilane (APTMS) or 3-aminopropyl triethoxysilane (APTES).

In another aspect the invention provides a method of making hybrid enzyme-silica nanoparticles (HES-NPs) comprising the steps of: (i) growing a siloxane scaffold around a silica-modified enzyme wherein the silyl groups seed the growth of the siloxane scaffold (e.g., in an emulsion or aqueous medium) to form hybrid enzyme-silica nanoparticles (HES-NPs); and (ii) isolating (e.g. from the emulsion or medium) the hybrid enzyme-silica nanoparticles.

In embodiments:
  step (i) comprises contacting the silica-modified enzyme with tetraethoxysilane under aqueous conditions and hydrolyzing (e.g., with ammonium hydroxide) silane groups to start the growth of the siloxane scaffold;

step (i) comprises contacting the silica-modified enzyme with tetraethoxysilane under reverse emulsion conditions and hydrolyzing silane groups to start the growth of the siloxane scaffold;

the method further comprises the antecedent steps of: a) reacting an acrylic compound (acryloyl derivative) with amine groups of an enzyme to covalently decorate the enzyme with enone groups; and b) coupling a silyl amine to the enone groups to covalently decorate the enzyme with silyl groups, forming a silica-modified enzyme, wherein embodiment: the acrylic compound comprises an acryloyl group and a N-hydroxysuccinimide group, such as N-acryloxysuccinimide or acrylate-polyethyleneglycol N-hydroxysuccinimide; and/or the silyl amine comprises a silyl ether group and an amine group, such as 3-aminopropyl trimethoxysilane (APTMS) or 3-aminopropyl triethoxysilane (APTES);

the enzyme is selected from catalase, superoxide dismutase, asparaginase, methioninase, carboxypeptidase G2 and luciferase;

the nanoparticles are of average size 20-100 nm or 20-50 nm or 100-200 diameter;

the nanoparticles are conjugated with targeting groups such as peptides or antibodies to target cancer cells;

the method further comprises the step of administering the nanoparticles to a person in need thereof, and particularly wherein:

the enzyme is catalase;

the nanoparticles provide a bioresponsive ultrasound contrast agent, and imaging the patient by ultrasound, such as wherein the enzyme is catalase, effective to generate $O_2$ bubbles;

the person has or is at (imminent, demonstrable) risk of reperfusion injury and the enzyme is catalase, effective to scavenge reactive oxygen species (ROS);

the person has leukemia (e.g. acute lymphoblastic leukemia, ALL) and the enzyme is asparaginase, effective to deplete asparagine; or the person has leukemia (e.g. acute lymphoblastic leukemia, ALL) and one enzyme is asparaginase, effective to deplete asparagine, and another enzyme in methioninase, effective to deplete methionine;

the person has cancer and the enzyme is methioninase, effective to deplete methionine in combination with or without chemotherapy; or the person has a hypoxic solid tumor and the enzyme is catalase, effective to oxygenate solid tumors for radiosensitization;

the person has a hypoxic solid tumor and the enzyme is catalase, the method further comprises the step of infusing safe levels of $H_2O_2$ to the person, effective to oxygenate the solid tumors for radiosensitization; and/or the person is, has been or will be administered a prodrug, and the enzyme is prodrug converting enzyme, effective to convert the prodrug to a therapeutic drug;

The invention includes all combinations of the recited particular embodiments as if each combination had been laboriously separately recited.

BRIEF DESCRIPTION OF THE DRAWINGS

FIG. 5. Representative characterization of HES-NP obtained by aqueous conditions with nanoparticle tracking analysis (NTA) and intensity-weighted dynamic light scattering (DLS) size distribution.

FIG. 6A. Activity of free catalase and CAT-HES-NP after incubation at 37° C. for 16 h with or without proteinase K.

FIG. 6B. Activity of free asparaginase and ASNase-HES-NP after incubation at 37° C. for 26 h with or without cathepsin B.

DESCRIPTION OF PARTICULAR EMBODIMENTS OF THE INVENTION

We disclose a novel hybrid approach to shielding enzymes. We first modify the enzyme surface with silica precursors and then proceed to deposit silica to a desired thickness while retaining its biological activity. An advantage of this approach is that we can control final nanoparticle size and desired enzyme activity per particle by incorporating one or more or different enzyme molecules to optimize delivery and efficacy. Unlike passive trapping of enzymes in hollow silica spheres that utilize templates ≥100 nanometers, our nanoparticles can be made as small as 20-50 nanometer to achieve optimal delivery and enzyme activity. In an embodiment we exemplify the method with catalase as a model enzyme because it can be used to detect tissues in oxidative stress using ultrasound imaging, can be used as an anti-oxidant, and its activity is easily measured using commercial assay kits. In another embodiment example, we used our method to encapsulate catalase and also to encapsulate asparaginase. Our novel approach is not enzyme-specific and can be applied to any enzymes. Other exemplary enzymes include but are not limited to superoxide dismutase, methioninase, carboxypeptidase G2 and luciferase.

The invention provides a method for coating enzymes in nanoporous silica that allows free access to small molecules substrates, but not larger molecules such as antibodies or immune cells to be used as a treatment or imaging tool without interacting with the immune system. This approach extends the enzyme's activity in vivo and limits or prevents immune reactions.

General procedure for the preparation and characterization of hybrid enzyme-silica nanoparticles (HES-NP):

Preparation of HES-NP

Figure 1:
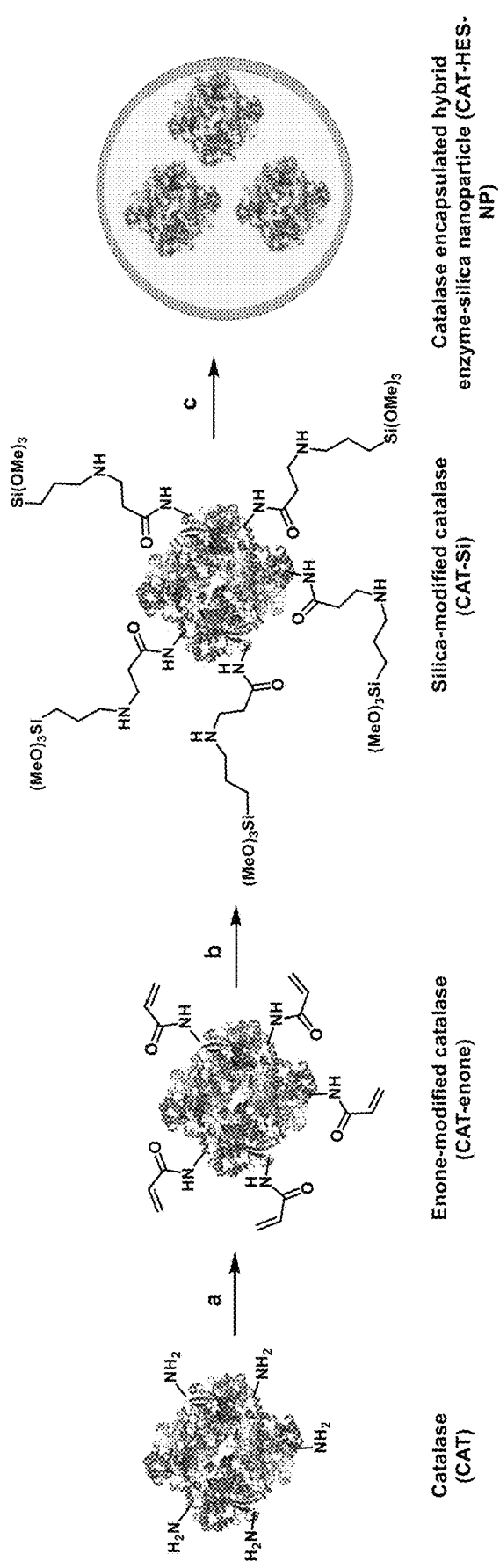
FIG. 1. Schematic representation of the preparation of hybrid enzyme-silica nanoparticles using catalase as a model enzyme (CAT-HES-NP).

Enzyme (i.e., catalase, superoxide dismutase, asparaginase, methioninase, etc.) (36 mg) was dissolved in sodium carbonate buffer (7.2 mL, 20 mM, pH 9.15) and a solution of N-acryloxysuccinimide (36 mg, in DMSO (72 µL) was added. The resulting mixture was stirred for 1 hour at room temperature and was purified by spin filtration in Amicon spin filters (Molecular weight Cutoff=10 kDa) at 4,000 g for 10 min. The filtrate was discarded, and the retentate was washed with water and spin filtered again at 4,000 g for 10 more minutes to yield the enone-modified enzyme (FIG. 1, step a). The purified enone-modified enzyme (3 mL, 12 mg/mL) was diluted down to a concentration of 1.5 mg/mL in 1M phosphate buffer pH 6.0 and water. (3-aminopropyl) trimethoxysilane (96 µL) was then added the resulting mixture was stirred for 1 hour at room temperature and purified by spin filtration in Amicon spin filters (Molecular weight Cutoff=10 kDa) at 4,000 g for 10 min. The filtrate was discarded, and the retentate was washed with water and spin filtered again at 4,000 g for 10 more minutes to yield the silica-modified enzyme (FIG. 1. Step b).

Before particle formulations, the silica-modified enzyme was filtered through a syringe filter (0.2 µm) to remove large aggregates. The silica-modified enzyme was then formulated into particles using two different formulations. The first method (aqueous conditions) yields nanoparticles around 100 nm or around 200 nm, and the second method (reverse emulsion) yield ultrasmall nanoparticles around 50 mm.

A] Aqueous Conditions

Tetraethoxysilane (240 µL) was added to the silica-modified enzyme solution in water (1.5 mg/mL, 2 mL). The resulting mixture was stirred vigorously for 10 minutes and ammonium hydroxide (7.2 µL of 28% $NH_4OH$ solution) was added to hydrolyze silane groups and start the silica particle growth. The resulting emulsion was stirred vigorously for 2 hours at room temperature particles were collected by high speed centrifugation at 20,000 g for 15 minutes. After this time, supernatant was discarded and pellets were redispersed in water (4 mL) for a second wash and centrifugation. The supernatant was discarded a second time and pelleted particles were dispersed in water for storage and characterization.

B] Reverse Emulsion Conditions

Tetraethoxysilane (142 µL) was added to the silica-modified enzyme solution (1.5 mg/mL, 500 µL) under reverse emulsion conditions with decane (oil phase, 28.409 mL), IGEPAL® CO-520 (surfactant, 2.318 mL) n-hexanol (co-surfactant, 784 µL). The resulting mixture was stirred vigorously for 10 minutes and ammonium hydroxide (71 µL of 28% $NH_4OH$ solution) was added to hydrolyze silane groups and start the silica particle growth. The resulting emulsion was stirred vigorously overnight at room temperature and ethanol (16 mL) was added to remove surfactants and precipitate the particles. The resulting bottom layer was extracted and submitted to high speed centrifugation at 20,000 g for 15 minutes. After this time, supernatant was discarded and pellets were redispersed in water (4 mL) for a second wash and centrifugation. The supernatant was discarded a second time and pelleted particles were dispersed in water for storage and characterization.

One-Pot Preparation of ASNase-HES-NP

Figure 3:
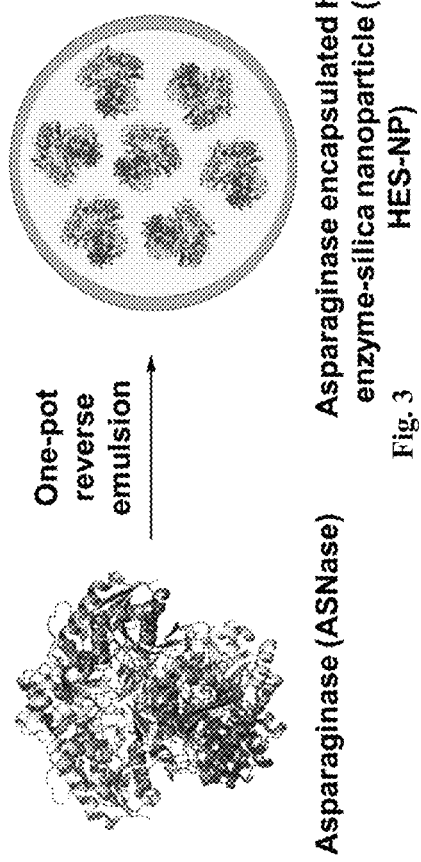
FIG. 3. Schematic representation of the preparation of hybrid asparaginase-silica nanoparticles using one-pot reverse emulsion conditions (ASNase-HES-NP).

ASNase-HES-NPs were prepared without surface functionalization (FIG. 3). Tetraethoxysilane (242 µL) was added to the enzyme solution (1 mg/mL, 500 µL) under reverse emulsion conditions with decane (oil phase, 28.409 mL), IGEPAL® CO-520 (surfactant, 2.318 mL), and n-hexanol (co-surfactant, 784 µL). The resulting mixture was stirred vigorously for 10 minutes and ammonium hydroxide (71 µL of 28% NH4OH solution) was added to hydrolyze silane groups and start the silica particle growth. The resulting emulsion was stirred vigorously overnight at room temperature and ethanol (10 mL) was added to remove surfactants and precipitate the particles. The resulting bottom layer was extracted and submitted to high speed centrifugation at 20,000 g for 15 minutes at 4° C. After this time, the supernatant was discarded, and pellets were redispersed in water (4 mL) for a second wash and centrifugation. The supernatant was discarded a second time and pelleted particles were dispersed in water for storage and characterization.

Characterization of HES-NP

Figure 2:
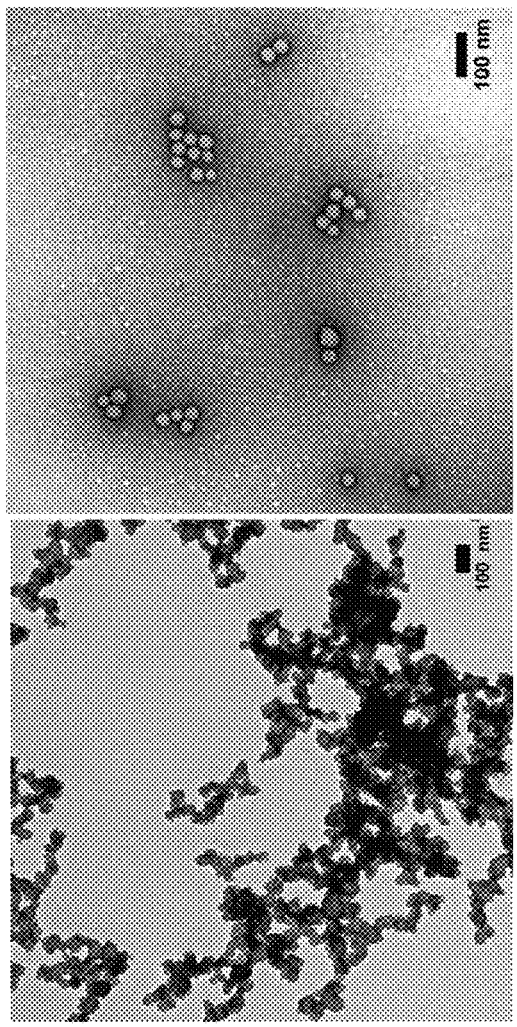
FIG. 2. Representative TEM images of LIES-NP produced under aqueous (left) or reverse emulsion (right) conditions.
Figure 4:
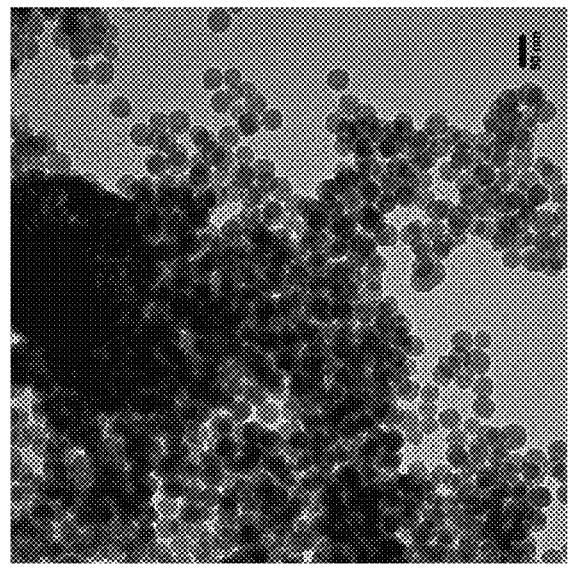
FIG. 4. Representative TEM image of ASNase-HES-NP produced under one-pot reverse emulsion conditions.

Nanoparticles were sonicated at 10° C. for three minutes in a bath sonicator before size measurements to prevent aggregation. Transmission electron microscopy (TEM, FEI Tecnai G2 Spirit transmission electron microscope equipped with a Gatan camera operating at 120 kV with. Digital Micrograph software) was performed with negative staining (2% uranyl acetate in water) on carbon-formvar coated copper grids. TEM pictures of CAT-HES-NP were taken and showed monodisperse particles for aqueous (FIG. 2, Left) and reverse emulsion conditions (FIG. 2, Right) with sizes between 30 and 60 mm Additionally, TEM pictures of ASNase-HES-NP were taken and showed monodisperse particles with approximate sizes of 50 nm (FIG. 4).

The hydrodynamic diameter of HES-NP was measured at 169.7 nm with a PdI of 0.159 by Dynamic Light Scattering (DLS, FIG. 5) (Zetasizer Z S, Malvern Instruments). HES-NP were measured with a mean diameter of 152.6 nm (StdDev=60) with a concentration of $7.6 \times 10^{11}$ NPs/mL by Nanoparticle Tracking Analysis (NTA, ZetaView, Particle Metrix, FIG. 5). The difference in size between the real size (TEM) and the size measured by DLS is explained by the higher scattering from larger molecules increasing the overall hydrodynamic diameter of the particle population.

Activity Measurements of CAT-HES-NP

The enzymatic activity of CAT-HES-NP (aqueous phase) was evaluated electrochemically to detect the first-order decomposition of $H_2O_2$ using a four-channel Free Radical. Analyzer (Item #TBR4100, World Precision instruments, Sarasota, Fla.) equipped with a $H_2O_2$ macro sensor (Item #: ISO-HPO-2). A standard curve using free CAT was created by measuring the current decay rate when known concentrations of $H_2O_2$ were added. Three different free CAT concentrations were used to construct the standard activity curves, to which the activity of CAT-HES-NP was compared. Briefly, the $H_2O_2$ sensor was equilibrated in PBS (1×) with stirring at 300 rpm. $H_2O_2$ (400 µL, 1 mM) was added into the PBS solution and shortly after, an aqueous solution of CAT (20 µL, 2 mg/mL) was added. Data collection was ended when the current reached zero. This process was repeated two more times with increasing concentrations of CAT (40 µL and 60 µL). Decay linearization was performed by taking the natural log of the linear portion of the current channel to obtain sample decay rates. Activity (U/mL) was calculated from the respective CAT volumes (Equation 1).

Activity (U/mL)=[CAT baseline activity (4,500 U/mg)*Concentration of CAT solution (mg/mL)*volume (µL)]/1000/Electrolyte volume (mL)   Equation 1

The decay rate (pA/s) was plotted against the corresponding activity (U/mL) to obtain the standard curve. The resulting slope of the standard curve (pA*mL/U*s) was used as the standard activity slope. The activity of CAT-HES-NP was measured in triplicate with the previously described method. From the standard curve, decay rate, and known dilution factors, the activity of the CAT-HES-NP was calculated. CAT-HES-NP have an average activity of 2,000 U/mL in 1 mg/mL (free CAT=4,500 U/mL in 1 mg/mL).

Stability Measurements of CAT-HES-NP

To confirm that enzyme-loaded silica nanoshells protect enzymes from inactivation by proteolysis, the activity of free enzyme and encapsulated enzyme was evaluated in the presence of proteinase K, a serine protease that cleaves a wide range of proteins. In this experiment, we used catalase as a model protein, as it is not expensive, allows facile observation of activity by naked eye (bubbles generated upon addition of $H_2O_2$) and quantitative measurement of the enzymatic activity using electrochemical detection. Specifically, we incubated free catalase and CAT-HES-NP overnight at 37° C. in pure water in the presence of $CaCl_2$ (10 mM, 50 μL) and proteinase K (50 μL at 1 mg/mL). After 16 h, free catalase kept only 6% of its activity, while CAT-HES-NP kept 87% of its activity (FIG. 6A). This slight activity loss is most likely due to the degradation of catalase attached at the surface of the particle.

Activity Measurements of ASNase-HES-NP

The enzymatic activity of ASNase-HES-NP was measured by colorimetric detection using Nessler's assay (Sigma Aldrich, EC 3.5.1.1). Nessler's reagent is a solution of potassium tetraiodomercurate(II) ($K_2[HgI_4]$) and potassium hydroxide that changes color in the presence of ammonia. Briefly, a solution of asparagine (25 μL, 189 mM) in Tris buffer (250 μL, 50 mM, pH=8.6) and water (225 μL) was equilibrated to 37° C. Solutions of ASNase or ASNase-HES-NP were added and further incubated at 37° C. for 30 min. After 30 min, the reaction was quenched with trichloroacetic acid (25 μL, 1.5 M). The resulting solution was diluted in a 96-well plate with water and Nessler's reagent (12.5 μL) was added. After 1 min, the absorbance was measured at 436 nm at room temperature. An ammonia standard curve was prepared by plotting absorbance at 436 nm versus ammonia concentration from ammonium sulfate standards. ASNase activity was determined from the measured absorbance of the sample and the ammonia standard curve. One unit of ASNase corresponds to the liberation of 1.0 μmol of ammonia from L-asparagine per minute at pH 8.6 at 37° C. ASNase-HES-NPs formulated using one-pot reverse emulsion conditions were measured to have activity of 375 U/mL in 1 mg/mL (specific activity of ASNase used for formulations=440 U/mL in 1 mg/mL).

Stability Measurements of ASNase-HES-NP

To confirm that asparaginase-loaded silica nanoshells is protected from inactivation by proteolysis, the activity of free enzyme and encapsulated enzyme was evaluated in the presence of cathepsin B, a lysosomal protease that is present in leukemic cells and degrades ASNase. Specifically, free ASNase (60 μL, 1 mg/mL) and ASNase-HES-NP (60 μL, 0.5 mg/mL) were incubated for 26 h at 37° C. in the presence of sodium citrate buffer (30 μL, 10 mM, pH=5) and cathepsin. B (30 μL, 0.5 mg/mL). After 26 h, free ASNase was completely depleted while ASNase-HES-NP retained 98% survival from control (FIG. 6B)

Radiolabeling CAT-HES-NP with $^{89}$Zr

First, CAT-HES-NP was modified with a mixture of mPEG-silane and silane-PEG-thiol for biodistribution studies. Briefly, tetraethoxysilane (240 μL) was added to the silica-modified enzyme solution in water (1.5 mg/mL, 2 mL). The resulting mixture was stirred vigorously for 10 minutes and ammonium hydroxide (7.2 μL of 28% $NH_4OH$ solution) was added to hydrolyze silane groups and start the silica particle growth. The resulting emulsion was stirred vigorously for 2 h at room temperature, then ammonium hydroxide (3.5 μL of 28% $NH_4OH$ solution) was added to increase the pH before a mixture of mPEG-silane (Creative PEGWorks, MW 2 k 250 μL, 20 mg/mL) and silane-PEG-thiol (NANOCS, MW 5 k, 200 μL, 10 mg/mL) in 95% v/v ethanol was added and stirred at room temperature for an additional 1 hour. Particles were collected by high speed centrifugation at 20,000 g for 15 minutes at 4° C. After this time, the supernatant was discarded, and pellets were redispersed in water (4 mL) for a second wash and centrifugation. The supernatant was discarded a second time and pelleted particles were dispersed in water. Then, the particles were conjugated with deferoxamine-maleimide (DFO-mal), a strong chelator to $^{89}$Zr. Briefly, DFO-mal (7.1 mg, 10 mop was dissolved in DMSO (50 μL) and stirred at room temperature overnight with CAT-HES-NP (2 mg/mL, 10 mL, 10 μmol silane-PEG-thiol). After 17 hours, the particles were purified via high-speed centrifugation (20,000 g, 15 min, 4° C.) and then concentrated 5 times and dispersed in PBS 1× (10 mg/mL, 5 mM DFO-mal, $3.5 \times 10^{12}$ NPs/mL).

CAT-HES-NPs were radiolabeled with $^{89}$Zr (half-life=3.3 days). Briefly, $^{89}$Zr oxalate (1.416 mCi) was added to CAT-HES-NP and stirred at 650 rpm for 2 h at 37° C. After 2 h, the particles were purified by spin filtration in. Amicon spin filters (Molecular weight Cutoff=10 kDa) and centrifuged at 4,000 g for 10 min. The retentate and filtrate activity was measured, and the filtrate was discarded. Pentetic acid (200 μL, 50 mM, pH=7) was added to the retentate to remove free $^{89}$Zr and then the spin filters were centrifuged. The retentate and filtrate activity was measured at this time and the filtrate was discarded. Then, PBS (1×, 400 μL) was added to the retentate and the spin filters were centrifuged. The filtrate activity was measured and then discarded. This process was repeated with PBS (1×). Finally, the radiolabeled particles were recovered by inverting the spin filters and centrifuging at 1,000 g for 2 min. The recovered particles were diluted to reach 100 μCi/mL. Three standards (9 μCi) were kept aside for decay corrections. The radiostability of the particles were assessed in fresh rat plasma and PBS (1×) using the previously described procedure. Radiolabeled CAT-HES-NP was radiostable up to 7 days in plasma and PBS (1×).

Biodistribution of $^{89}$Zr-CAT-HES-NP in Tumor-Bearing Mice

Figure 7A:
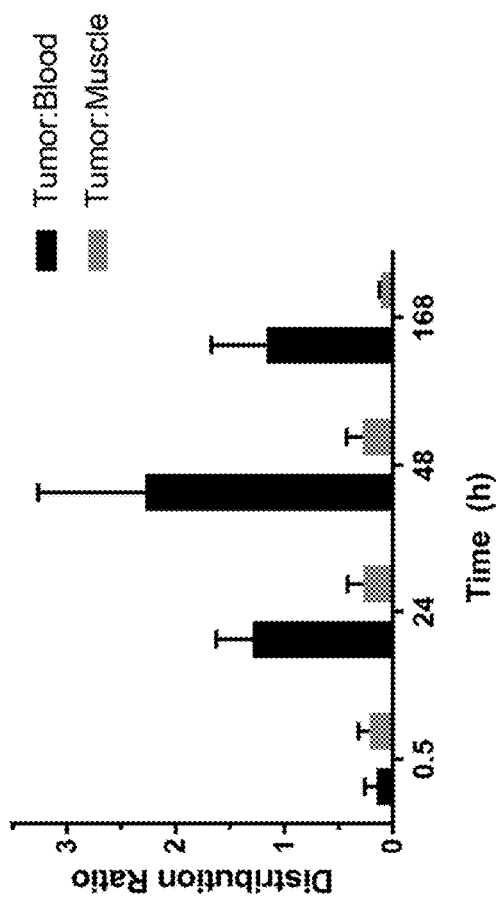
FIG. 7A. Biodistribution of $^{89}$Zr-CAT-HES-NP in tumor-bearing mice expressed as percent injected dose per gram of tissue.
Figure 7B:
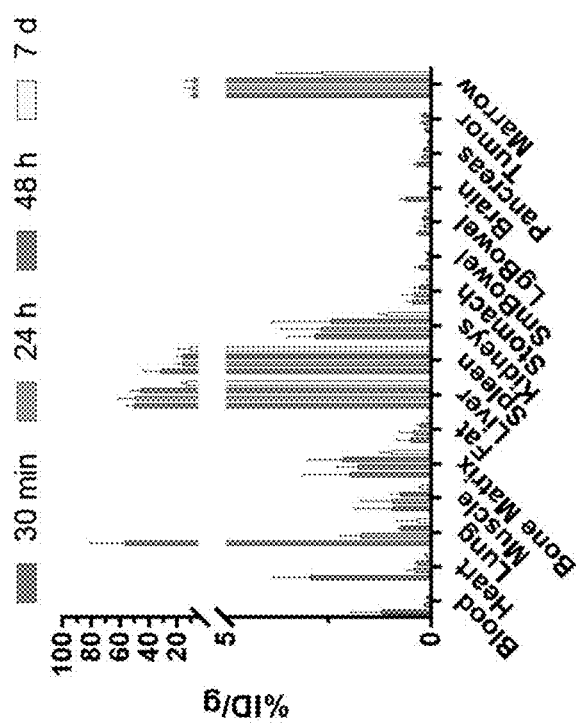
FIG. 7B. Passive tumor uptake of $^{89}$Zr-CAT-HES-NP relative to blood and muscle over time.

Nude mice were injected with $1 \times 10^6$ MC-38 tumor cells in the flank and tumors were allowed to grow for 10 days. After 10 days, tumor-bearing mice were intravenously injected in the tail vein with $^{89}$Zr-CAT-HES-NPs (10 μL, 10±1 μCi) and were sacrificed at 30 min (N=4), 24 h (N=4), 48 h (N=5), and 7 d (N=4). The animals were dissected, organs were removed and weighed, and radioactivity in each organ and tumor was measured with a gamma counter. The percent injected dose per gram of tissue (% ID/g) over time showed preferential accumulation in the lung, liver, spleen, kidneys, and bone marrow (FIG. 7A). The particle accumulation in the tumor relative to blood and muscle increased over time, demonstrating passive tumor uptake (FIG. 7B)

Acute Kidney Injury (AM) Model with CAT-HES-NP

Figure 8:
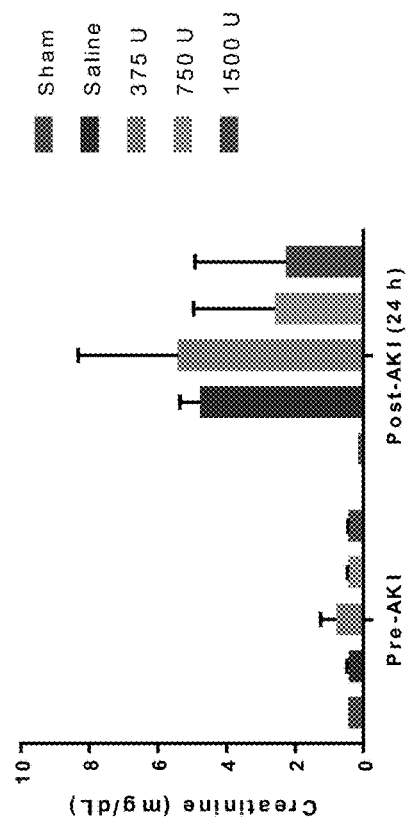
FIG. 8. Creatinine levels 24 hours post-AKI with three doses of CAT-HES-NP.

An in vivo AKI model was carried out in female Sprague Dawley rats to assess the potential of scavenging reactive oxygen species by CAT-HES-NP in the event of ischemic reperfusion, ultimately providing a protective effect for the kidney. Nephrectomies were performed in the right kidney 7 days prior to the AKI as the presence of both kidneys could normalize the serum blood urea nitrogen (BUN) and creatinine (Cr) values used to assess renal function. Blood and urine samples were collected for baseline values, then CAT-HES-NP was administered intravenously via tail vein 5 min before AKI was produced in the left renal artery by occlusion for 60 min. This experiment included 5 groups: saline as a positive control (N=2), sham as a negative control (N=1), and 3 treatment groups (377, 754, and 1508 U) with N=3 each. Blood and urine samples were collected at 24 hours post-AKI to assess recovery. CAT-HES-NPs in PBS (1×) were sonicated for at least 5 min to minimize aggregation before injection. The resulting Cr levels 24 hours post-AKE suggests a protective effect with a positive dose response (FIG. 8).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A method of making hybrid enzyme-silica nanoparticles (HES-NPs), comprising the steps of:
    a) reacting acryloyl groups of acrylic compounds with amine groups of enzymes to covalently decorate the enzymes with enone groups;
    b) coupling silyl amines to the enone groups to covalently decorate the enzymes with silyl groups, forming silica-modified enzymes;
    c) growing siloxane scaffolds around the silica-modified enzymes, wherein the silyl groups seed the growth of the siloxane scaffolds to form the hybrid enzyme-silica nanoparticles, with each of the nanoparticles comprising a nanoporous silica shell encapsulating a plurality of the silica-modified enzymes; and
    d) isolating the hybrid enzyme-silica nanoparticles.

2. The method of claim 1, wherein the acrylic compounds comprises an acryloyl group and a N-hydroxysuccinimide group.

3. The method of claim 1, wherein the silyl amines are 3-aminopropyl trimethoxysilane (APTMS) or 3-aminopropyl triethoxysilane (APTES).

4. The method of claim 2, wherein the silyl amines are 3-aminopropyl trimethoxysilane (APTMS) or 3-aminopropyl triethoxysilane (APTES).

5. The method of claim 1, wherein the enzymes are selected from catalase, superoxide dismutase, asparaginase, methioninase, carboxypeptidase G2 and luciferase.

6. The method of claim 4, wherein the enzymes are selected from catalase, superoxide dismutase, asparaginase, methioninase, carboxypeptidase G2 and luciferase.

7. The method of claim 1, wherein the shell is spherical and has a porosity that allows free access to small molecule substrates of the enzymes, while excluding proteases, antibodies and immune cells.

8. The method of claim 1, wherein step (c) comprises contacting the silica-modified enzymes with tetraethoxysilane under surfactant-free aqueous conditions and hydrolyzing silane groups to start the growth of the siloxane scaffolds.

9. The method of claim 1, wherein step (c) comprises contacting the silica-modified enzymes with tetraethoxysilane under reverse emulsion conditions and hydrolyzing silane groups to start the growth of the siloxane scaffolds.

10. The method of claim 1, wherein the nanoparticles are of average size 20-50 nm-diameter.

11. The method of claim 1, wherein the nanoparticles are conjugated with targeting groups comprising peptides or antibodies to target cancer cells.

12. The method of claim 1, wherein the enzymes are selected from catalase, superoxide dismutase, asparaginase, methioninase, carboxypeptidase G2 and luciferase.

13. The method of claim 7, wherein:
    the acrylic compounds comprise an acryloyl group and a N-hydroxysuccinimide group; and
    the silyl amines are 3-aminopropyl trimethoxysilane (APTMS) or 3-aminopropyl triethoxysilane (APTES).

14. The method of claim 7, wherein:
    the acrylic compounds comprises an acryloyl group and a N-hydroxysuccinimide group;
    the silyl amines are 3-aminopropyl trimethoxysilane (APTMS) or 3-aminopropyl triethoxysilane (APTES); and
    the enzymes are selected from catalase, superoxide dismutase, asparaginase, methioninase, carboxypeptidase G2 and luciferase.

15. The method of claim 1, further comprising the step of administering the nanoparticles to a person in need thereof.

16. The method of claim 1, further comprising the steps of administering the nanoparticles to a person in need thereof, the enzyme in the hybrid enzyme-silica nanoparticle is catalase.

17. The method of claim 1, further comprising the step of administering the nanoparticles to a person in need thereof, wherein the nanoparticles provide a bioresponsive ultrasound contrast agent, and imaging the patient by ultrasound.

18. The method of claim 1, further comprising the step of administering the nanoparticles to a person in need thereof, wherein the person has or is at demonstrable risk of reperfusion injury and the enzyme in the hybrid enzyme-silica nanoparticle is catalase, effective to scavenge reactive oxygen species (ROS).

19. The method of claim 1, further comprising the step of administering the nanoparticles to a person in need thereof, wherein:
    the person has leukemia and the enzyme is asparaginase and/or methioninase, effective to deplete asparagine and/or methioninase, or
    the person has cancer and the enzyme is methioninase, effective to deplete methionine in combination with or without chemotherapy; or
    the person has a hypoxic solid tumor and the enzyme is catalase, effective to oxygenate solid tumors for radiosensitization; or
    the person has a hypoxic solid tumor and the enzyme is catalase, the method further comprises the step of infusing $H_2O_2$ to the person, effective to oxygenate the solid tumors for radiosensitization.

20. The method of claim 1, further comprising the step of administering the nanoparticles to a person in need thereof, wherein the person is administered a prodrug prior to, concomitant with, or after administration of the nanoparticles, and the enzyme is prodrug converting enzyme, effective to convert the prodrug to a therapeutic drug.

* * * * *